(12) United States Patent
Kim et al.

(10) Patent No.: US 10,945,637 B2
(45) Date of Patent: Mar. 16, 2021

(54) IMAGE BASED JAUNDICE DIAGNOSING METHOD AND APPARATUS AND IMAGE BASED JAUNDICE DIAGNOSIS ASSISTING APPARATUS

(71) Applicant: AJOU UNIVERSITY INDUSTRY-ACADEMIC COOPERATION FOUNDATION, Suwon-si (KR)

(72) Inventors: Jin Hong Kim, Yongin-si (KR); Myung Hoon Sunwoo, Seoul (KR); Jung Won Lee, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 431 days.

(21) Appl. No.: 15/855,504

(22) Filed: Dec. 27, 2017

(65) Prior Publication Data
US 2018/0177434 A1 Jun. 28, 2018

(30) Foreign Application Priority Data

Dec. 28, 2016 (KR) .................. 10-2016-0181212
Oct. 13, 2017 (KR) .................. 10-2017-0133524

(51) Int. Cl.
*A61B 5/103* (2006.01)
*G06T 7/00* (2017.01)
(Continued)

(52) U.S. Cl.
CPC .......... *A61B 5/1034* (2013.01); *A61B 5/1455* (2013.01); *A61B 5/14546* (2013.01);
(Continued)

(58) Field of Classification Search
CPC ... A61B 5/1034; A61B 5/6898; A61B 5/1455; A61B 5/14546; A61B 5/7264;
(Continued)

(56) References Cited

U.S. PATENT DOCUMENTS

| | | | |
|---|---|---|---|
| 2007/0172155 A1* | 7/2007 | Guckenberger | G06F 16/583 382/305 |
| 2008/0008370 A1* | 1/2008 | Chio | G06T 7/0012 382/128 |

(Continued)

FOREIGN PATENT DOCUMENTS

| | | |
|---|---|---|
| JP | 2015-9140 A | 1/2015 |
| JP | 2016-516475 A | 6/2016 |

(Continued)

OTHER PUBLICATIONS

Communication dated Jan. 28, 2019, issued by the Korean Patent Office in counterpart Korean Patent Application No. 10-2017-0133524.

(Continued)

Primary Examiner — Sanjay Cattungal
(74) Attorney, Agent, or Firm — Sughrue Mion, PLLC

(57) ABSTRACT

Disclosed are image based jaundice analyzing method and apparatus. The image based jaundice analyzing method according to an exemplary embodiment of the present disclosure includes: receiving an image for jaundice diagnosis obtained by photographing a specific body part of a user and a reference object in a location where the user is currently located; generating color distortion information representing a degree of color distortion of the reference object included in the image for jaundice diagnosis; generating a correction image for jaundice diagnosis by correcting the color distortion of the image for jaundice diagnosis based on the color distortion information; and diagnosing a (Continued)

jaundice symptom of the user using the correction image for jaundice diagnosis.

16 Claims, 7 Drawing Sheets

(51) Int. Cl.
*G06T 7/90* (2017.01)
*A61B 5/1455* (2006.01)
*A61B 5/145* (2006.01)
*A61B 5/00* (2006.01)

(52) U.S. Cl.
CPC .......... *A61B 5/6898* (2013.01); *G06T 7/0012* (2013.01); *G06T 7/90* (2017.01); *A61B 5/0077* (2013.01); *A61B 5/7264* (2013.01); *A61B 2576/00* (2013.01); *G06T 2207/10024* (2013.01); *G06T 2207/30041* (2013.01)

(58) Field of Classification Search
CPC . A61B 5/0077; A61B 2576/00; G06T 7/0012; G06T 7/90; G06T 2207/10024; G06T 2207/30041
See application file for complete search history.

(56) References Cited

U.S. PATENT DOCUMENTS

| | | | |
|---|---|---|---|
| 2010/0145731 A1* | 6/2010 | Benja-Athon | G06Q 50/22 705/3 |
| 2012/0065089 A1* | 3/2012 | Kuno | G01N 33/57407 506/9 |
| 2012/0253166 A1* | 10/2012 | Ahn | A61B 5/015 600/407 |
| 2015/0057551 A1* | 2/2015 | Chou | A61B 5/1032 600/477 |

FOREIGN PATENT DOCUMENTS

| | | |
|---|---|---|
| KR | 10-2015-0107565 A | 9/2015 |
| KR | 10-2015-0128916 A | 11/2015 |

OTHER PUBLICATIONS

Communication dated May 30, 2017, issued by the Korean Patent Office in counterpart Korean Patent Application No. 10-2016-0181212.

* cited by examiner

[FIG. 1]
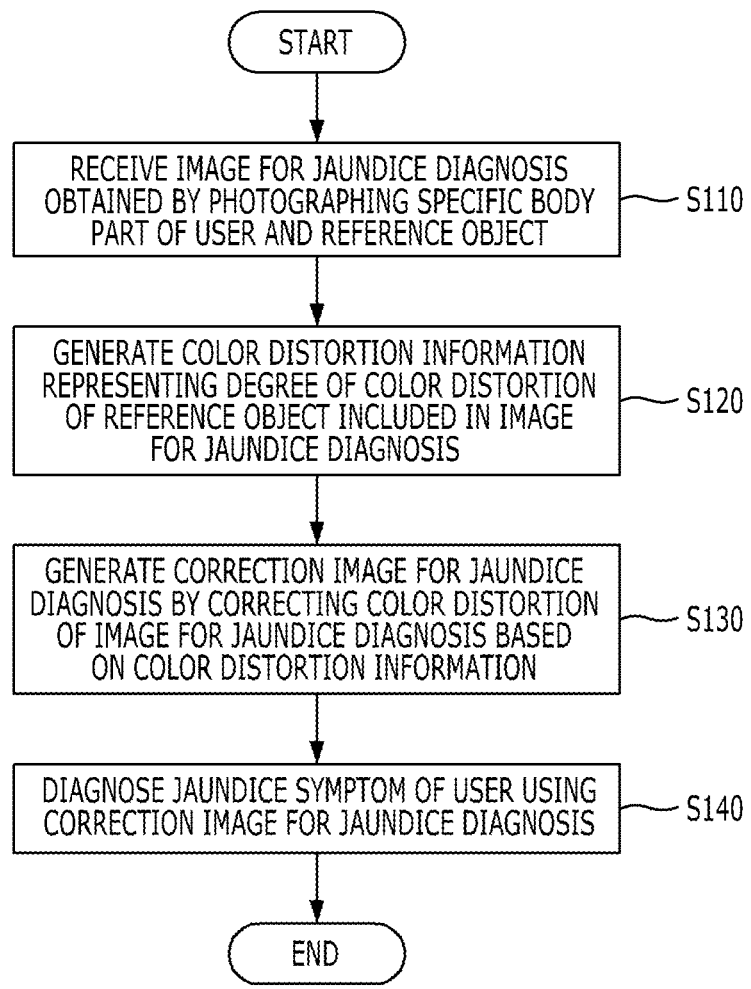

[FIG. 2]
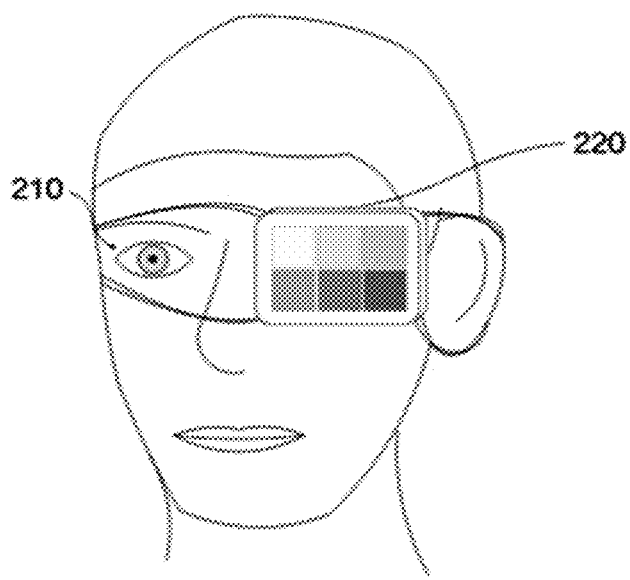
[FIG. 3]
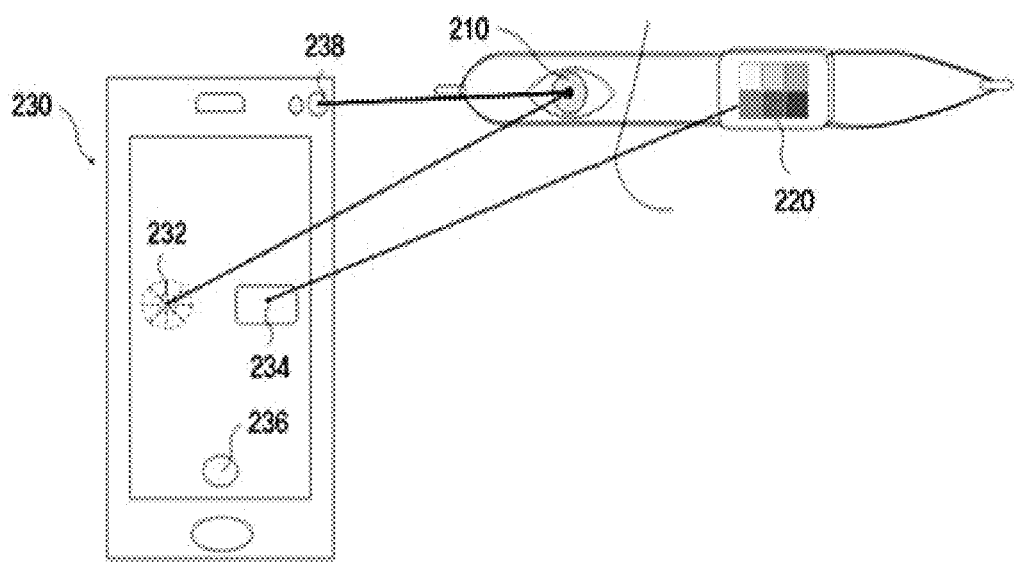

[FIG. 4A]
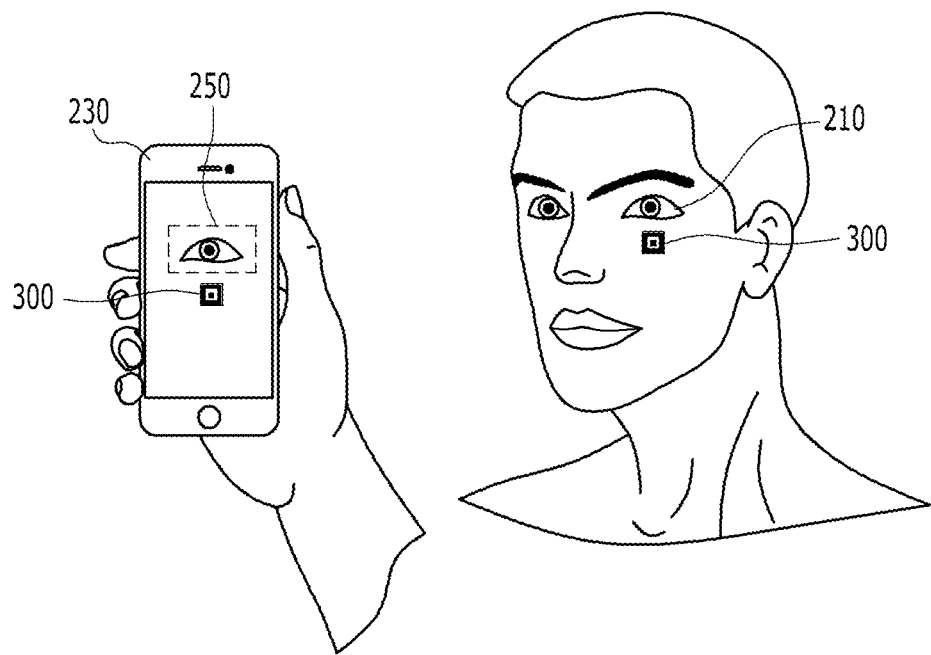
[FIG. 4B]
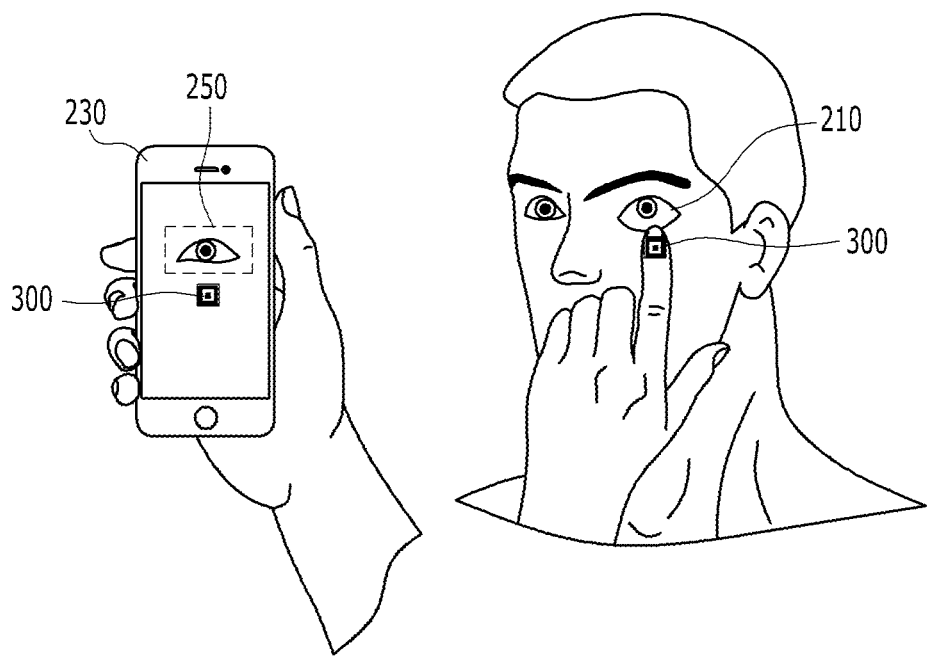

[FIG. 5A]
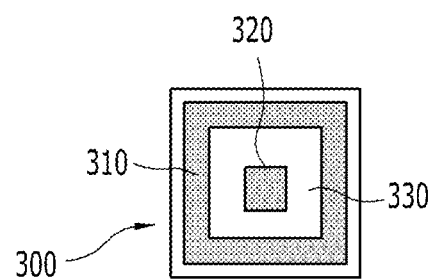
[FIG. 5B]
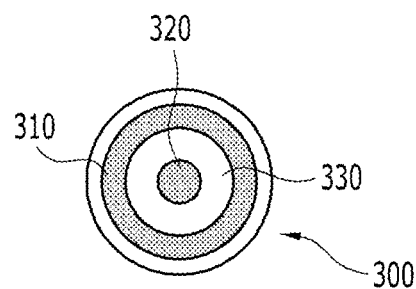

[FIG. 6]
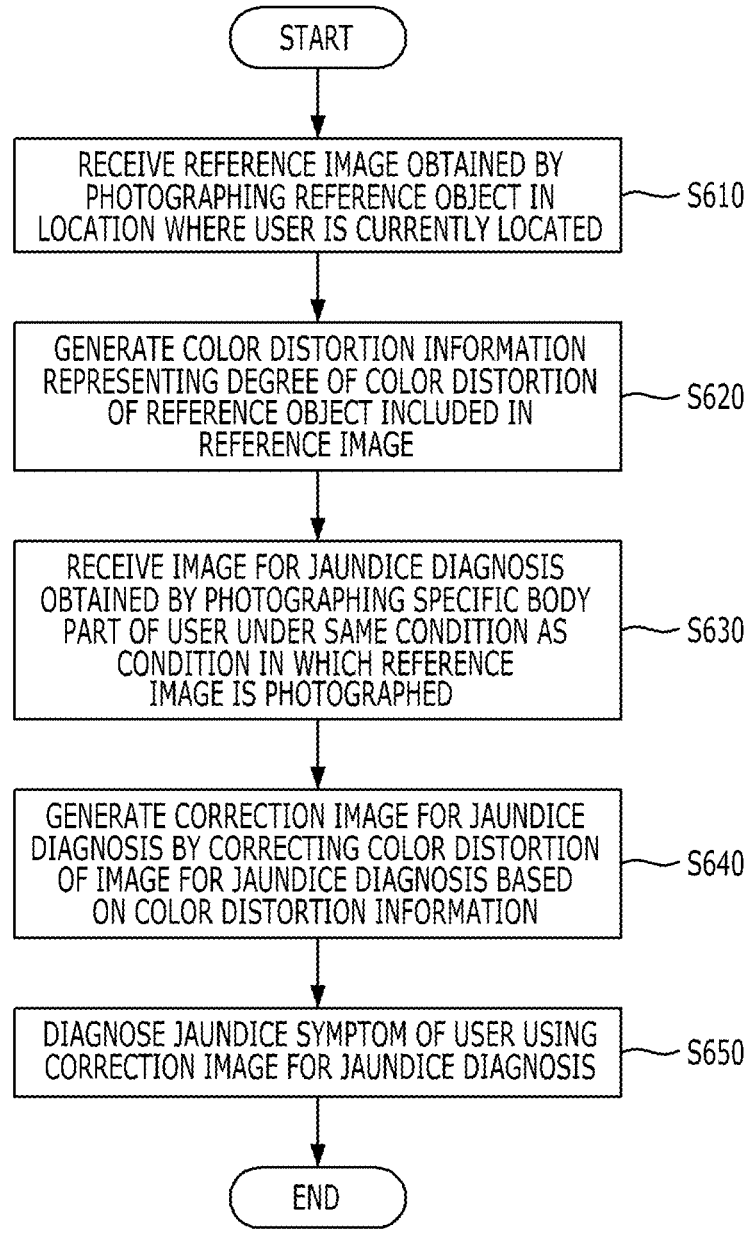

[FIG. 7]
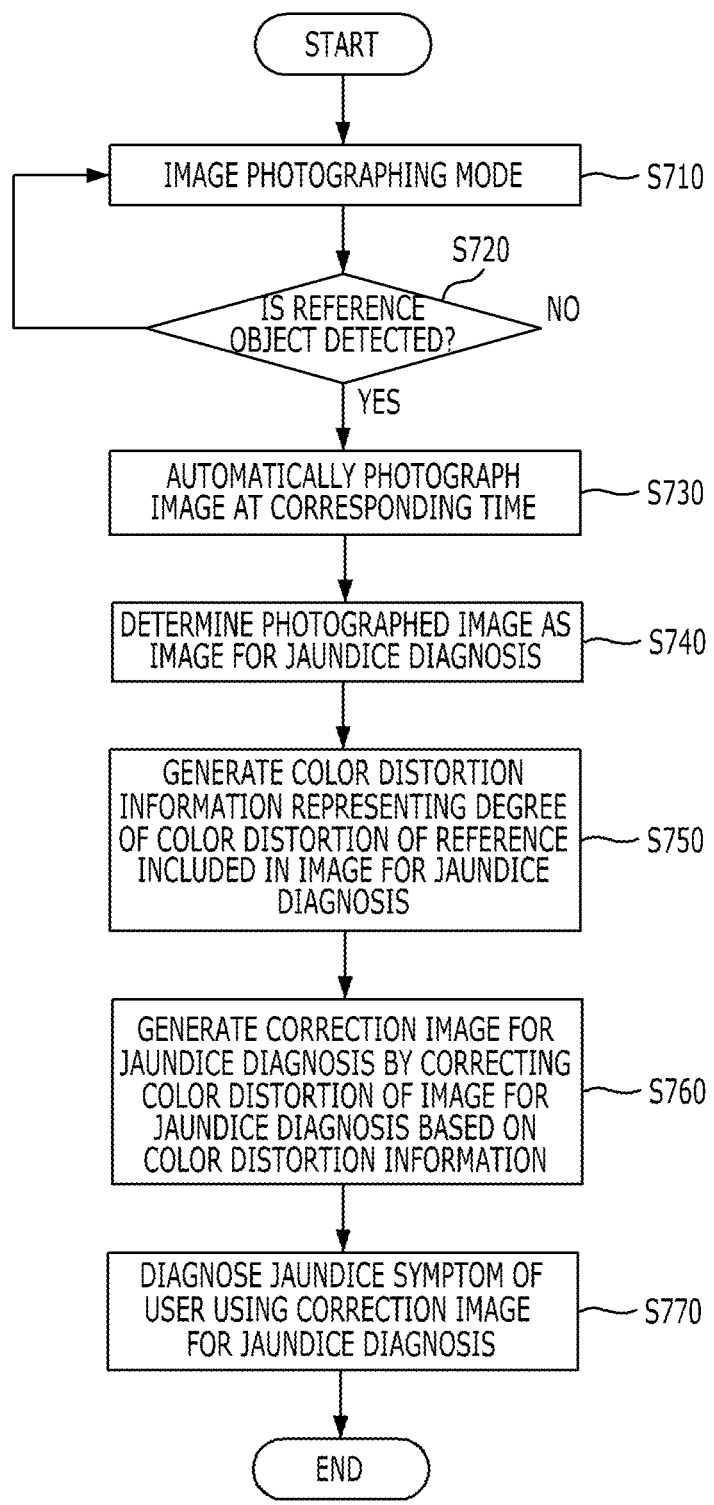

[FIG. 8]
800
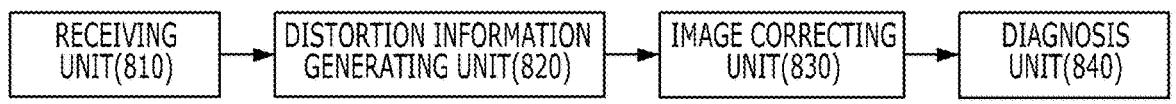
[FIG. 9]
900
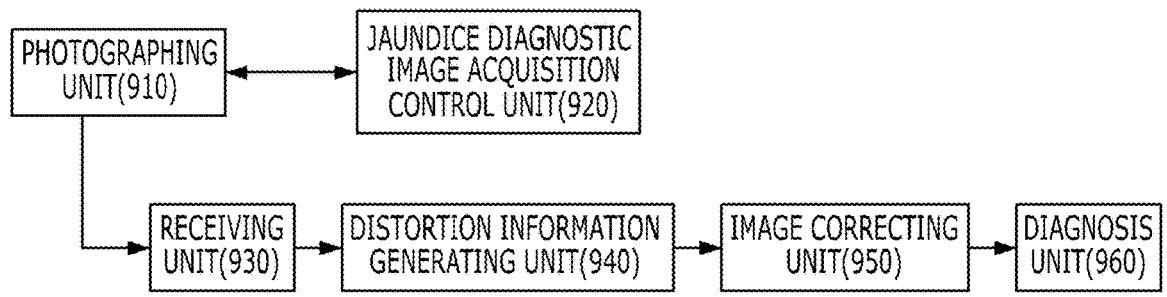
[FIG. 10]
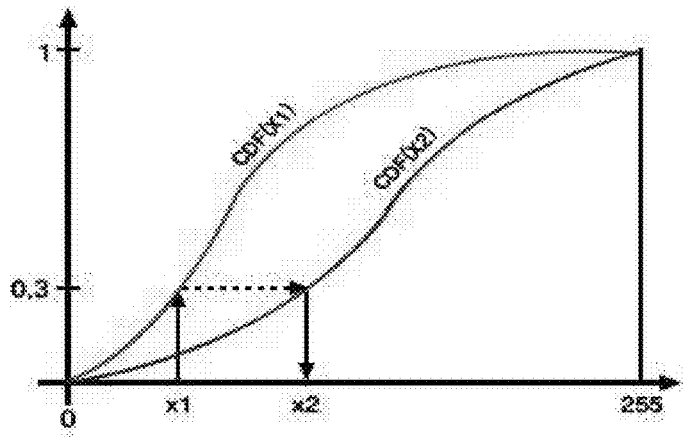
[FIG. 11]
1100

IMAGE BASED JAUNDICE DIAGNOSING METHOD AND APPARATUS AND IMAGE BASED JAUNDICE DIAGNOSIS ASSISTING APPARATUS

CROSS-REFERENCE TO RELATED APPLICATIONS

This application claims the priority of Korean Patent Application Nos. 10-2016-0181212 and 10-2017-0133524 filed on Dec. 28, 2016 and Oct. 13, 2017, respectively, in the Korean Intellectual Property Office, the disclosure of which is incorporated herein by reference.

BACKGROUND

Field

The present disclosure relates to jaundice diagnosis, and more particularly, to an image based jaundice diagnosing method and apparatus.

Description of the Related Art

Jaundice refers to yellowish pigmentation of the white of eye (sclera), the skin, the mucous membrane, or the like, due to excess accumulation of yellow bile pigment (bilirubin) which is produced during decomposition of a special protein including iron such as hemoglobin in the body.

However, diagnostic methods for diagnosing the jaundice based on a scientific view or a serological test of the related art have some problems. When the jaundice is diagnosed through visual examination which is a scientific examination which diagnoses the jaundice with the naked eye, there is a problem in that the jaundice may not be objectively diagnosed, but may be subjectively diagnosed. Accordingly, in order to confirm the jaundice, the patient's blood needs to be sampled to measure bilirubin in the blood. Further, the patient with suspected jaundice needs to visit a medical facility equipped with a device which is capable of measuring the bilirubin to confirm the jaundice and it takes time to obtain the test result value after sampling the blood.

Further, the patient with jaundice needs to periodically revisit the hospital to check for signs of illness during the treatment period. However, when the patient lives far from the medical facility or it is hard to periodically visit the medical facility due to the condition of the patient, accessibility to the medical service may be lowered.

Further, when lesion image data is obtained through an external device such as a smart phone, color of the lesion part may be distorted due to various external environments such as illumination, and there is a difficulty to obtain image data which is precisely focused due to an external factor such as hand shaking of a photographer.

RELATED ART DOCUMENT (Patent Document) Korean Unexamined Patent Application Publication No. 10-2014-0108649 (entitled Video game to monitor retinal diseases, published on Sep. 12, 2014)

SUMMARY

An object of the present disclosure is to provide an image based jaundice diagnosing method and apparatus which remotely diagnose the jaundice of a user.

Another object of the present disclosure is to provide an image based jaundice diagnosing method and apparatus which suppress an external factor such as hand shaking generated during a process of obtaining an image and correct color distortion of a lesion part caused due to various illumination environments.

Technical objects of the present disclosure are not limited to the aforementioned technical objects and other technical objects which are not mentioned will be apparently appreciated by those skilled arts from the following description.

According to an aspect of the present disclosure, there is provided a method for diagnosing jaundice based on an image by a jaundice diagnosing apparatus including: receiving an image for jaundice diagnosis obtained by photographing a specific body part of a user and a reference object; generating color distortion information representing a degree of color distortion of the reference object included in the image for jaundice diagnosis; generating a correction image for jaundice diagnosis by correcting the color distortion of the image for jaundice diagnosis based on the color distortion information; and diagnosing a jaundice symptom of the user using the correction image for jaundice diagnosis.

The diagnosing of a jaundice symptom of the user may include transmitting a jaundice diagnosis request which includes the correction image for jaundice diagnosis and requests the jaundice diagnosis for the user to a diagnosis server; and receiving a jaundice diagnosis result which is a diagnosis result for the jaundice diagnosis request from the diagnosis server.

The jaundice diagnosis result may be determined based on the image analysis result for the correction image for jaundice diagnosis and also determined further selectively based on at least one of medical history information of the user and medical treatment information of others with a jaundice symptom.

The jaundice diagnosis result may further include health risk information indicating whether the jaundice symptom of the user is risky for health, based on the correlation between the disease of the user predicted based on at least one of the medical history information of the user and the medical treatment information of others and the image analysis result.

When the reference object is a white object, in the generating of color distortion information, color temperature difference information which is a difference value between a first color temperature of the reference object in a reference image obtained by photographing the reference object under a previously stored reference light source and a second color temperature of the reference object included in the image for jaundice diagnosis may be generated and in the generating of a correction image for jaundice diagnosis, the color temperature of the image for jaundice diagnosis may be corrected such that the color temperature of the reference object of the image for jaundice diagnosis is equal to the first color temperature based on the color temperature difference information to generate a correction image for jaundice diagnosis.

The specific body part of the user may include at least one of a face and an eyeball of the user.

The method may further include outputting a user interface for photographing the image for jaundice diagnosis, in which in the receiving of an image for jaundice diagnosis, the image photographed based on a photographing guideline provided on the user interface in real time may be received.

The image for jaundice diagnosis may be an image in which the reference object is worn or attached on the specific body part of the user.

The reference object may be an eye patch and the eye patch may be configured by a single area having a white color or a plurality of areas having different colors.

The reference object may be an attachable patch and the attachable patch may be configured by a plurality of areas having a white color and at least one different color.

In the attachable patch, a pattern in which a first area and a second area having the same color are alternately disposed with a white area therebetween may be formed.

The attachable patch may be attached on a face within a predetermined distance from the eye of the user or attached to a tool within a predetermined distance from the eye when a tool is used to widen a sclera of the eye.

The method may further include before the receiving of an image for jaundice diagnosis, analyzing an image displayed through a photographing unit equipped in the jaundice diagnosing apparatus in real time to automatically photograph an image at a time when the reference object is detected, in which the photographed image may be an image for jaundice diagnosis.

The color distortion information may be generated based on at least one of illumination of environment in which the image for jaundice diagnosis is photographed, a photographic related setting value of a user device which photographs the image for jaundice diagnosis and a lens aberration of a lens mounted on the user device.

When a reference image obtained by photographing the reference object under a reference light source which is stored in advance has a YCbCr format and the image for jaundice diagnosis has an RGB format, the generating of color distortion information may include generating a converted image for jaundice diagnosis by converting the image for jaundice diagnosis into the YCbCr format; and calculating a first luminance distribution function which is a cumulative probability density function for a luminance value Y of the entire pixels belonging to a converted image for jaundice diagnosis to generate the color distortion information, in the generating of a correction image for jaundice diagnosis, the correction image for jaundice diagnosis may be generated by correcting the converted image for jaundice diagnosis corresponding to the first luminance distribution function to have a second luminance distribution function which is a cumulative probability density function for a luminance value Y of entire pixels belonging to the reference image.

According to another aspect of the present disclosure, there is provided an image based jaundice diagnosing apparatus including: a receiving unit which receives an image for jaundice diagnosis obtained by photographing a specific body part of a user and a reference object; a distortion information generating unit which generates color distortion information representing a degree of color distortion of the reference object included in the image for jaundice diagnosis; an image correcting unit which corrects the color distortion of the image for jaundice diagnosis based on the color distortion information to generate a correction image for jaundice diagnosis; and a diagnosis unit which diagnoses a jaundice symptom of the user using the correction image for jaundice diagnosis.

According to another aspect of the present disclosure, there is provided an image based jaundice diagnosis assisting apparatus, including: a receiving unit which receives a correction image for jaundice diagnosis in which color distortion is corrected as an image obtained by photographing a specific body part of the user and a reference object; a searching unit which searches medical history information of the user from a patient medical history DB including medical history information of a plurality of patients with jaundice; and an output unit which outputs the searched medical history information of the user and the correction image for jaundice diagnosis.

The image based jaundice diagnosis assisting apparatus may further include: an analyzing unit which analyzes the correction image for jaundice diagnosis to generate an image analysis result indicating whether the user has a jaundice symptom and a depth of the jaundice, in which the output unit further outputs the image analysis result.

According to the exemplary embodiment of the present disclosure, the jaundice of the patient is remotely diagnosed, so that it is possible to reduce time and economic wastage generated when a user who does not have a jaundice symptom visits the hospital and also reduce working hours of a doctor because the doctor does not need to unnecessarily give a medical treatment for a user who does not have a jaundice symptom.

Further, according to another exemplary embodiment of the present disclosure, the doctor is provided with a diagnosis result for a jaundice symptom which is automatically calculated based on an image for jaundice diagnosis, medical history information of the user, and medical treatment information of others with the jaundice symptom, as assistant materials, to diagnose and prescribe the jaundice so that burden of the medical treatment of the doctor may be reduced.

According to another exemplary embodiment of the present disclosure, the user may be diagnosed with the jaundice symptom at any time, thereby enabling early diagnosis of the disease.

According to still another exemplary embodiment of the present disclosure, a patch which is used as an assistant tool for photographing an image is used as an assistant unit for automatic focus recognition and also corrects color distortion of a lesion part which is photographed under various illumination environments, thereby improving a quality of image data which is utilized for diagnosis and medical treatment of a doctor.

Technical effects of the present invention are not limited to the above-mentioned technical effects, and other technical effects, which are not mentioned above, can be clearly understood by those skilled in the art from the following descriptions.

BRIEF DESCRIPTION OF THE DRAWINGS

The above and other aspects, features and other advantages of the present disclosure will be more clearly understood from the following detailed description taken in conjunction with the accompanying drawings, in which:

FIG. 1 is a flowchart for explaining an image based jaundice diagnosing method according to an exemplary embodiment of the present disclosure;

FIG. 2 is a view for explaining a method for obtaining an image for jaundice diagnosis according to an exemplary embodiment of the present disclosure;

FIG. 3 is a view for explaining a user interface according to an exemplary embodiment of the present disclosure;

FIGS. 4A and 4B is a view for explaining a method for obtaining an image for jaundice diagnosis according to another exemplary embodiment of the present disclosure;

FIGS. 5A and 5B is an exemplary diagram for explaining a patch illustrated in FIGS. 4A and 4B;

FIG. 6 is a flowchart for explaining an image based jaundice diagnosing method according to another exemplary embodiment of the present disclosure;

FIG. 7 is a flowchart for explaining an image based jaundice diagnosing method according to still another exemplary embodiment of the present disclosure;

FIG. 8 is a view for explaining an image based jaundice diagnosing apparatus according to an exemplary embodiment of the present disclosure;

FIG. 9 is a view for explaining an image based jaundice diagnosing apparatus according to another exemplary embodiment of the present disclosure;

FIG. 10 is a view for explaining a method for generating a correction image for jaundice diagnosis using a luminance distribution function according to an exemplary embodiment of the present disclosure; and FIG. 11 is a view for explaining an image based jaundice diagnosis assisting apparatus according to an exemplary embodiment of the present disclosure.

DETAILED DESCRIPTION OF THE PREFERRED EMBODIMENT

Those skilled in the art may make various modifications to the present invention and the present invention may have various embodiments thereof, and thus specific embodiments will be illustrated in the drawings and described in detail in detailed description. However, this does not limit the present invention within specific exemplary embodiments, and it should be understood that the present invention covers all the modifications, equivalents and replacements within the spirit and technical scope of the present invention. In the description of respective drawings, similar reference numerals designate similar elements.

Terms such as first or second, A or B may be used to describe various components but the components are not limited by the above terms. The above terms are used only to discriminate one component from the other component. For example, without departing from the scope of the present invention, a first component may be referred to as a second component, and similarly, a second component may be referred to as a first component. A term of and/or includes combination of a plurality of related elements or any one of the plurality of related elements.

It should be understood that, when it is described that an element is "coupled" or "connected" to another element, the element may be directly coupled or directly connected to the other element or coupled or connected to the other element through a third element. On the contrary, it should be understood that when an element is referred to as being "directly connected to" or "directly coupled to" another element, another element does not intervene therebetween.

Terms used in the present application are used only to describe specific exemplary embodiments, and are not intended to limit the present invention. A singular form may include a plural form if there is no clearly opposite meaning in the context. In the present disclosure, it should be understood that term "include" or "have" indicates that a feature, a number, a step, an operation, a component, a part or the combination thoseof described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

Hereinafter, exemplary embodiments according to the present disclosure will be described in detail with reference to accompanying drawings.

FIG. 1 is a flowchart for explaining an image based jaundice diagnosing method according to an exemplary embodiment of the present disclosure.

In step 110, a jaundice diagnosing apparatus receives an image for jaundice diagnosis obtained by photographing a specific body part of a user and a reference object together.

In this case, the image for jaundice diagnosis may be an image photographed at a location where the user is currently located and the specific body part of the user may be a face or an eyeball of the user or a body part of the user such as a wrist by which a skin of the user can be checked.

Further, the reference object may be an object which is a reference for correcting a color of the face skin or the eyeball of the user and may be a white object such as a white paper, a white post-it, a white fabric, a white plastic model, a white hat, a white band, or white glasses or may be a color band, a color chart, or a patch which is configured by a plurality of colors.

Further, the image for jaundice diagnosis may be acquired by photographing the reference object which is held by a user in the hand or photographing the reference object after disposing the reference object near the body part of the user or photographing the reference object which is worn or attached on the specific body part of the user.

For example, the reference object may be an eye patch which is configured by a single area having a white color or a plurality of areas having different colors, which will be described below with reference to FIG. 2. Further, the reference object may be a patch which is configured by a plurality of areas having white color and at least one different color, which will be described below with reference to FIGS. 4A and 4B, FIGS. 5A and 5B.

In the meantime, the reason why the specific body part of the user and the reference object are photographed together to generate the image for jaundice diagnosis is that a color of the user's body part may be distorted according to the environment (particularly, the illumination environment) of the location where the user's body part is photographed.

For example, when the user with a jaundice symptom visits a doctor's office of the hospital to photograph the eyeball of the user under fluorescent light and thereafter the eyeball of the user is photographed under the incandescent lamp at the user's home, even though the color of the eyeball of the user does not actually change, the eyeball of the user in the image photographed under the incandescent lamp is more yellowish. Therefore, since there is a necessity for correcting the color distortion as described above, an image for jaundice diagnosis obtained by photographing the reference object together is generated.

According to another exemplary embodiment, when the image for jaundice diagnosis is photographed, the user may use a user interface for photographing an image for jaundice diagnosis provided by the jaundice diagnosing apparatus, which will be described below with reference to FIG. 3.

In step 120, the jaundice diagnosing apparatus generates color distortion information representing a degree of color distortion of the reference object included in the image for jaundice diagnosis.

In this case, the color distortion information may be generated based on the illumination of the environment in which the image for jaundice diagnosis is photographed, a photographic related setting value (a diaphragm value, a shutter speed, ISO, or the like) of a user device which photographs the image for jaundice diagnosis, and a lens aberration of a lens mounted on the user device.

Here, the user device may include all devices having a photographing function of photographing an image of the user and a communication function of transmitting the image for jaundice diagnosis to the outside, such as a smart phone, a portable phone, a notebook, or a desktop computer of the user. The jaundice diagnosing apparatus may be a user device or a device mounted on the user device.

In this case, the color distortion information may be information based on a color temperature.

More specifically, the jaundice diagnosing apparatus may generate color temperature difference information which is a difference value between a first color temperature which is a color temperature of the reference object in a reference image obtained by photographing a reference object (or the reference object and the specific body part of the user) under a predetermined reference light source and a second color temperature which is a color temperature of the reference object included in the image for jaundice diagnosis, as the color distortion information.

Here, the reference light source may be a virtual light source which has a specific color temperature (5600 K or 3200 K) as a reference or an actual light source of the doctor's office of the hospital that the user visited.

For example, when the reference object is an A4-size white paper, a first color temperature value which is a color temperature for the A4-size white paper in the reference image obtained by photographing the A4-size white paper under a light source having a specific color temperature as a reference is already known. Therefore, the jaundice diagnosing apparatus may generate color temperature difference information which is a difference value between the first color temperature value and the second color temperature which is a color temperature of the reference object included in the image for jaundice diagnosis to generate color distortion information. In this case, instead of storing the reference image in advance, the jaundice diagnosing apparatus may store only the first color temperature for the A4-size white paper in advance.

Further, in the case of the reference image which is generated by photographing the reference object in the doctor's office of the hospital or photographing the reference object and the user together when the user with a jaundice symptom visits the hospital, the reference light source is a light source provided in the doctor's office of the hospital and the color temperature of the reference object in the reference image is the first color temperature.

In another exemplary embodiment, the color distortion information may be information based on luminance Y.

For example, when the reference image has a YCbCr format and the image for jaundice diagnosis has an RGB format, the jaundice diagnosing apparatus converts the image for jaundice diagnosis with an RGB format into the YCbCr format to generate a converted image for jaundice diagnosis and then calculates a first luminance distribution function which is a cumulative probability density function for a luminance value Y of entire pixels belonging to the converted image for jaundice diagnosis to be generated as color distortion information.

In step 130, the jaundice diagnosing apparatus corrects the color distortion of the image for jaundice diagnosis based on the color distortion information to generate a correction image for jaundice diagnosis.

In this case, when the color distortion information is the color temperature difference information, the jaundice diagnosing apparatus corrects the color temperature of the image for jaundice diagnosis such that the color temperature of the reference object of the image for jaundice diagnosis is equal to the first color temperature, based on the color temperature difference information, to generate the correction image for jaundice diagnosis.

Further, when the color distortion information is a first luminance distribution function, the jaundice diagnosing apparatus calculates a second luminance distribution function which is a cumulative probability density function for the luminance value Y of the entire pixels belonging to the reference image with the YCbCr format and corrects the image for jaundice diagnosis corresponding to the first luminance distribution function to have the second luminance distribution function to generate the correction image for jaundice diagnosis.

This will be described below with reference to FIG. 10.

FIG. 10 is a view for explaining a method for generating a correction image for jaundice diagnosis using a luminance distribution function according to an exemplary embodiment of the present disclosure.

Referring to FIG. 10, a CDF(x1) graph represents the first luminance distribution function corresponding to the image for jaundice diagnosis which needs to be corrected, a CDF (x2) graph represents the second luminance distribution function corresponding to the reference image, a horizontal axis represents a luminance value, and a vertical axis represents a cumulative probability density value.

In FIG. 10, a process of correcting the first luminance distribution function to be equal to the second luminance distribution function is a process of converting a luminance value of a pixel in the first luminance distribution function (the CDF (x1) graph) into a luminance value of a pixel in the second luminance distribution function (the CDF(x2) graph) having the same cumulative probability density value.

For example, when the luminance value of the pixel x1 in the first luminance distribution function (CDF(x1) graph) is corrected, a pixel x2 which is a pixel having a cumulative probability density value which is equal to 0.3 which is a cumulative probability density value of a pixel x1 is found from the second luminance distribution function (CDF(x2) graph) and the luminance value of the pixel x1 is converted into the luminance value of the pixel x2.

In step 140, the jaundice diagnosing apparatus diagnoses a jaundice symptom of the user using the correction image for jaundice diagnosis.

Desirably, when the jaundice symptom for the user is diagnosed, the jaundice diagnosing apparatus transmits a jaundice diagnosis request which includes the correction image for jaundice diagnosis and requests the jaundice diagnosis for the user to a diagnosis server (for example, a server equipped in the hospital) and receives a jaundice diagnosis result which is a diagnosis result for the jaundice diagnosis request from the diagnosis server to perform the diagnosis.

In another exemplary embodiment, the jaundice diagnosing apparatus may directly analyze the correction image for jaundice diagnosis to perform the jaundice diagnosis, instead of transmitting the correction image for jaundice diagnosis to the diagnosis server.

In the meantime, the diagnosis server may determine the jaundice diagnosis result based on the image analysis result for the correction image for jaundice diagnosis.

In still another exemplary embodiment, the diagnosis server may determine the jaundice diagnosis result not only based on the image analysis result, but also based on medical history information of the user and medical treatment information of others with a jaundice symptom.

In this case, the diagnosis server estimates a disease of the user based on at least one of the medical history information of the user and the medical treatment history of others and generates a jaundice diagnosis result including health risk information indicating whether the jaundice symptom of the user is risky for health, based on the correlation between the predicted disease of the user and the image analysis result. For example, a degree of health risk of the jaundice symptom when the user suffers from a disease A may be higher than a degree of health risk of the jaundice symptom when the user suffers from a disease B. Therefore, even though a user suffers from the same degree of jaundice symptom, if the user suffers from the disease A, it may be determined that the degree of health risk is high and if the user suffers from the disease B, it may be determined that the degree of health risk is not high.

In this case, the jaundice diagnosing apparatus may output a message requesting to quickly visit the hospital to the user who suffers from the disease A because the degree of health risk is high.

In the meantime, the disease that the user suffers from may be automatically predicted by machine learning based on the medical history information of the user and the medical treatment information of others or may be directly determined by a doctor.

Further, the jaundice diagnosis result may be automatically determined by image analysis and various data analysis as described above or may be determined by a doctor using image analysis and various data analysis results as assistant materials. In this case, the doctor may diagnose and prescribe the jaundice symptom also in consideration of the medical history information of the user so that diagnosis and prescription personalized for a patient may be provided.

As described above, according to the exemplary embodiment of FIG. 1, there is an advantage in that when the user does not visit the hospital in advance or after first visit of the hospital to photograph the reference object and the specific body part of the user, the user's jaundice symptom may be remotely diagnosed without visiting the hospital to diagnose the jaundice symptom every time.

FIG. 2 is a view for explaining a method for obtaining an image for jaundice diagnosis according to an exemplary embodiment of the present disclosure.

Referring to FIG. 2, a scene in which the user wears an eye patch 220 which is configured by a plurality of areas having different colors on its' own eyeball 210 and photographs an image for jaundice diagnosis is illustrated. In this case, the eye patch 220 may be configured by a plurality of areas having different colors or may be configured by a single area having a white color.

As described above, when the reference object is the eye patch 220, there is an advantage in that the user easily wears the eye patch to photograph an image. In the meantime, when the jaundice diagnosing apparatus receives an image for jaundice diagnosis photographed as illustrated in FIG. 2, the jaundice diagnosing apparatus corrects the image for jaundice diagnosis based on the colors corresponding to the plurality of areas included in the eye patch 220 to generate a correction image for jaundice diagnosis.

For example, the jaundice diagnosing apparatus calculates an RGB pixel difference value by subtracting RGB pixel values for the colors under the reference light source from the RGB pixel values for colors included in the image for jaundice diagnosis and then adds the calculated RGB pixel difference value to the RGB pixel values of the pixels included in the image for jaundice diagnosis to generate the correction image for jaundice diagnosis.

Next, the jaundice diagnosing apparatus transmits the correction image for jaundice diagnosis to the diagnosis server.

Next, the diagnosis server extracts all or a part of the pixels corresponding to the eyeball or the face skin of the user to select jaundice pixels whose pixel values belong to a section of the RGB pixel value corresponding to the jaundice from the extracted pixels.

Finally, the jaundice diagnosing apparatus compares a ratio of the jaundice pixels among the pixels extracted from the eyeball or the face skin of the user with at least one threshold value to diagnose whether the user has a jaundice symptom and a depth of jaundice.

For example, when a ratio of jaundice pixels is 50% or higher, it is diagnosed that the user has a jaundice symptom and when a ratio of jaundice pixels is 80% or higher, it is diagnosed that the jaundice is serious. If necessary, the user of the jaundice diagnosing apparatus may change the threshold value.

FIG. 3 is a view for explaining a user interface according to an exemplary embodiment of the present disclosure.

Referring to FIG. 3, user interfaces 232, 234, and 236 for photographing an image for jaundice diagnosis are output on a user device 230. The user adjusts the eyeball 210 to an eyeball area 232 displayed by a circle on an upper left side of the user device 230 and adjusts the eye patch 220 of the user to an eye patch area 234 of an upper right side of the user device 230 and then clicks a photographing button 236 on a lower side to photograph an image for jaundice diagnosis.

In this case, the user photographs the image for jaundice diagnosis in accordance with a photographing guideline provided from the user interfaces 232, 234, and 236 in real time.

For example, when the user is too close to the user device, the user interfaces 232, 234, and 236 may display a message instructing the user to step back a little and when the eyeball 210 of the user is too small to recognize, the user interfaces 232, 234, and 236 may display a message instructing the user to open the eyes wide.

Further, the user may adjust a focus with respect to the photographing object using the photographing button 236 or adjust the size of the eyeball area 232 and the eye patch area 234 on the user interfaces 232, 234, and 236.

FIGS. 4A and 4B is a view for explaining a method for obtaining an image for jaundice diagnosis according to another exemplary embodiment of the present disclosure and FIGS. 5A and 5B is an exemplary diagram for explaining a patch illustrated in FIGS. 4A and 4B.

FIG. 4A illustrates a scene in which the user attaches a patch 300 configured by color areas having a white color and at least one different color on a face of the user and photographs the image for jaundice diagnosis. Here, even though it is illustrated that the patch 300 is attached below the eye, the patch 300 may be attached on any other body part.

FIG. 4B illustrates a scene in which when the user strains an area below the eye with the fingers to make the sclera part of the eyeball more visible, the user attaches the patch 300 on a fingernail of the finger which strains the area below the eye and photographs the image for jaundice diagnosis. Here, even though fingers are used to widen a range of the sclera of the eyeball, in addition to the fingers, any tools which may widen the range of the sclera of the eyeball may be used.

When the tool is used, the patch 300 may be attached within a predetermined distance from the eye. In this case, the tool may include the fingers.

In the meantime, the patch 300 which is attached for jaundice diagnosis is used as an assistant tool for correcting color distortion of the photographed image caused by the performance difference of different cameras for individuals and the surrounding environments and photographing an in-focus image and is configured by a plurality of areas having a white color and at least one different color. The patch may be an attachable type. Therefore, the patch 300 may be configured such that the color areas having white color and at least one different color are disposed on a front surface and an attachment area is formed on a rear surface to be attachable. In the color area disposed on the front surface, the white area may be used as a reference for correcting the color of the image for jaundice diagnosis and the remaining color areas may be used as a reference for obtaining an in-focus image. For example, a pattern in which a first area and a second area having the same color are alternately disposed with the white area therebetween may be formed on the front surface of the patch 300. Further, the patch 300 needs to be detachable from the body (for example, the face) of the user or the tool and photographed together with the specific body part of the user so that the patch 300 may have an arbitrary size appropriate for attachment to the body part (for example, the face) of the user or the tool. For example, the patch 300 be a size of 10-won coin or a size of a pupil. Further, the patch may have various shapes such as a rectangle, a circle, or an oval.

Referring to FIGS. 5A and 5B, FIG. 5A illustrates a rectangular patch and FIG. 5B illustrates a circular patch. The patch 300 may have a pattern in which a white area 330 is disposed between a first black area 310 and a second black area 320. Here, the first and second black areas 310 and 320 are used to obtain an in-focus image and the white area 330 may be used as a reference for correcting the color of the image for jaundice diagnosis. Even though, in FIGS. 5A and 5B, a patch 300 having a color area in which the first black area 310 and the second black area 320 are alternately disposed with the white area 330 therebetween to easily discern the patch 300 from the other body part (for example, the eyeball) has been illustrated, the color area of the patch 300 may be configured by various forms.

Hereinafter, a method for diagnosing the jaundice when the user attaches the patch 300 as illustrated in FIGS. 5A and 5B on the own specific body part will be described. When a photographing unit is driven to diagnose the jaundice, the jaundice diagnosing apparatus 230 (or a user device) equipped with the photographing unit analyzes an image which is displayed through the photographing unit before photographing the image in real time to detect the patch 300 and determines an image at the time of detecting the patch 300 as an in-focus image to automatically photograph the image. In this case, the photographed image may be an image for jaundice diagnosis.

That is, the jaundice diagnosing apparatus 230 analyzes the image which is displayed through the photographing unit before photographing the image in real time, and detects edges of the first black area 310 and the second black area 320 using an edge detecting algorithm. In this case, as the edge detecting algorithm, various algorithms such as a canny edge detector algorithm, a Roberts edge detecting algorithm, a sobel edge detecting algorithm, or a prewitt edge detecting algorithm may be used.

When the edges of the first black area 310 and the second black area 320 are detected, the jaundice diagnosing apparatus determines that the image is an in-focus image and automatically photographs the image at that time. Further, when the edges of the first black area 310 and the second black area 320 are detected, the jaundice diagnosing apparatus 350 determines whether the detected edges are within a predetermined range of the image. When the detected edges are in the predetermined range, the jaundice diagnosing apparatus 350 determines the image as an in-focus image and automatically photographs the image at that time. Here, the predetermined range may be a range with respect to a center of the image.

In this case, the jaundice diagnosing apparatus 230 may provide the photographing guideline through a user interface or a voice to photograph the in-focus image. For example, when the user is too close to the user device, the jaundice diagnosing apparatus 230 may output a message instructing the user to step back a little and when the eyeball 210 of the user is too small to recognize, may output a message instructing the user to open the eyes wide. Further, when the first black area 310 is detected in a partially cut state, the jaundice diagnosing apparatus 230 may output a message instructing the user to move to a direction where all edges of the first black area 310 and the second black area 320 are detected. Further, when the edges of the first black area 310 and the second black area 320 are not within a predetermined range of the image, the jaundice diagnosing apparatus 230 may output a message instructing the user to move to be located within a predetermined range.

As described above, when the reference object is the patch 300, the patch may be easily attached by the user and the jaundice diagnosing apparatus 230 (or the user device) automatically photographs the image for jaundice diagnosis so that the user does not need to press the photographing button to photograph an image for jaundice diagnosis.

When the image for jaundice diagnosis is photographed, the jaundice diagnosing apparatus 230 corrects the image for jaundice diagnosis based on the white color included in the patch 300 of the image for jaundice diagnosis to generate a correction image for jaundice diagnosis. That is, the jaundice diagnosing apparatus 300 calculates a pixel difference value by subtracting a pixel value for the white color under the reference light source from the pixel value of the white area and then adds the calculated pixel difference value to each RGB pixel value of the pixels included in the image for jaundice diagnosis to generate the correction image for jaundice diagnosis.

The jaundice diagnosing apparatus 300 transmits the correction image for jaundice diagnosis to the diagnosis server.

By doing this, the diagnosis server extracts all or a part of the pixels corresponding to the eyeball or the face skin of the user to select jaundice pixels whose pixel values belong to a section of the RGB pixel value corresponding to the jaundice, from the extracted pixels. In this case, the diagnosis server searches for a predetermined range with respect to the position of the patch to determine a position of a region of interest for jaundice diagnosis and extract the pixels in the region of interest. Further, the region of interest may be set in advance and the diagnosis server may extract pixels of the set region of interest which has been set in advance. For example, an eye area may be set as the region of interest. Further, when the user directly sets the region of interest in the image for jaundice diagnosis, the diagnosis server may extract pixels of the selected region of interest.

Finally, the jaundice diagnosing apparatus 300 compares a ratio of the jaundice pixels among the pixels extracted from the eyeball or the face skin of the user with at least one threshold value to diagnose whether the user has a jaundice symptom and a depth of jaundice.

In the jaundice diagnosing apparatus 300 which performs the operation as described above, an application for jaundice diagnosis may be installed. Therefore, when the user executes the application for jaundice diagnosis, a photographic mode is automatically driven and the image for jaundice diagnosis is photographed only when the patch is detected. Therefore, the user does not need to press the photographing button to photograph an image.

FIG. 6 is a flowchart for explaining an image based jaundice diagnosing method according to another exemplary embodiment of the present disclosure.

In step 610, the jaundice diagnosing apparatus receives a reference image obtained by photographing a reference object in a location where the user is currently located.

In step 620, the jaundice diagnosing apparatus generates color distortion information representing a degree of color distortion of the reference object included in the reference image.

This exemplary embodiment is different from the exemplary embodiment of FIG. 1 in that the color distortion information is generated using the reference image obtained by photographing the reference object in a location where the user is currently located.

In this case, the color distortion information may be generated based on color temperature difference information or using a luminance distribution function as described above.

In step 630, the jaundice diagnosing apparatus receives an image for jaundice diagnosis obtained by photographing a specific body part of the user under the same condition as the condition of photographing the reference image.

In this case, the same photographing condition means that the image is photographed using the same light source under the same surrounding environment in the same location.

In step 640, the jaundice diagnosing apparatus corrects the color distortion of the image for jaundice diagnosis based on the color distortion information to generate a correction image for jaundice diagnosis.

In this case, the image for jaundice diagnosis is photographed under the same condition as the reference image so that even when the color distortion of the image for jaundice diagnosis is corrected using the color distortion information generated using the reference image, the color distortion may be effectively corrected.

In step 650, the jaundice diagnosing apparatus diagnoses a jaundice symptom of the user using the correction image for jaundice diagnosis.

FIG. 7 is a flowchart for explaining an image based jaundice diagnosing method according to still another exemplary embodiment of the present disclosure.

When an image photographic mode of the photographing unit is driven in step 710, the jaundice diagnosing apparatus analyzes an image which is displayed through the photographing unit before photographing the image in step 720 to determine whether the reference object is detected.

That is, the jaundice diagnosing apparatus analyzes the image displayed through the photographing unit before photographing an image in real time to determine whether an edge of a patch which is set in advance is detected. For example, the jaundice diagnosing apparatus detects an edge of the remaining area of the color area of the patch except the white area.

In step 730, when the edge of the reference object is detected, the jaundice diagnosing apparatus determines that the image at the time when the edge is detected is an in-focus image to automatically photograph the image at that time.

In step 740, the jaundice diagnosing apparatus determines the image photographed in step 730 as the image for jaundice diagnosis. The image for jaundice diagnosis may include the specific body part of the user and the reference object.

In step 750, the jaundice diagnosing apparatus generates color distortion information representing a degree of color distortion of the reference object included in the image for jaundice diagnosis. In this case, the color distortion information may be generated based on color temperature difference information or using a luminance distribution function as described above.

For example, when the reference object is an attachable patch as illustrated in FIGS. 5A and 5B, a first color temperature which is a color temperature of the patch for the white color is already known from the reference image obtained by photographing a patch under a light source having a specific color temperature as a reference. Therefore, the jaundice diagnosing apparatus generates color temperature difference information which is a difference value between the first color temperature value and a second color temperature which is a color temperature of a patch included in the image for jaundice diagnosis for the white color to generate the color distortion information. In this case, instead of storing the reference image in advance, the jaundice diagnosing apparatus may store only the first color temperature for the white color in advance.

In step 760, the jaundice diagnosing apparatus corrects the color distortion of the image for jaundice diagnosis based on the color distortion information to generate a correction image for jaundice diagnosis.

In step 770, the jaundice diagnosing apparatus diagnoses a jaundice symptom of the user using the correction image for jaundice diagnosis.

FIG. 8 is a view for explaining an image based jaundice diagnosing apparatus according to an exemplary embodiment of the present disclosure.

Referring to FIG. 8, a jaundice diagnosing apparatus 800 according to an exemplary embodiment of the present disclosure includes a receiving unit 810, a distortion information generating unit 820, an image correcting unit 830, and a diagnosis unit 840.

The receiving unit 810 receives an image for jaundice diagnosis obtained by photographing a specific body part of the user and a reference object in a location where the user is currently located.

The distortion information generating unit 820 generates color distortion information representing a degree of color distortion of the reference object included in the image for jaundice diagnosis.

The image correcting unit 830 corrects the color distortion of the image for jaundice diagnosis based on the color distortion information to generate a correction image for jaundice diagnosis.

The diagnosis unit 840 diagnoses a jaundice symptom of the user using a correction image for jaundice diagnosis.

In this case, the diagnosis unit 840 may include a transmitting unit (not illustrated) and a result processing unit (not illustrated).

The transmitting unit transmits a jaundice diagnosis request which includes the correction image for jaundice diagnosis and requests jaundice diagnosis for the user to a diagnosis server (not illustrated).

In another exemplary embodiment, instead of transmitting the jaundice diagnosis request to the diagnosis server, the transmitting unit may directly transmit the correction image for jaundice diagnosis to a device of a doctor.

In this case, the device of the doctor includes all devices having a communication function which is capable of receiving the correction image for jaundice diagnosis such as a smart phone, a mobile phone, a notebook, or a desktop computer of the doctor and a display function which is capable of outputting the correction image for jaundice diagnosis.

When the jaundice diagnosis result which is a diagnosis result for the jaundice diagnosis request is received from the diagnosis server (not illustrated) through the receiving unit 810, the processing unit diagnoses the jaundice of the user using the jaundice diagnosis result. Desirably, the jaundice diagnosing apparatus 800 according to the exemplary embodiment of the present disclosure may further include a user interface management unit (not illustrated) which outputs a user interface for photographing an image for jaundice diagnosis.

The jaundice diagnosing apparatus 800 according to another exemplary embodiment will be operated as follows.

The receiving unit 810 receives a reference image obtained by photographing a reference object in a location where the user is currently located.

The distortion information generating unit 820 generates color distortion information representing a degree of color distortion of the reference object included in the reference image.

When the image for jaundice diagnosis obtained by photographing the specific body part of the user under the same condition as a condition in which the reference image is photographed is received through the receiving unit 810, the image correcting unit 830 corrects the color distortion of the image for jaundice diagnosis based on the color distortion information to generate the correction image for jaundice diagnosis.

The diagnosis unit 840 diagnoses a jaundice symptom of the user using a correction image for jaundice diagnosis.

The jaundice diagnosing apparatus 800 according to still another exemplary embodiment of the present invention will be operated as follows.

The receiving unit 810 receives a reference eyeball image obtained by photographing the eyeball of the user in a first location in which a photographing condition is known and receives an image for jaundice diagnosis obtained by photographing the eyeball of the user in a second location other than the first location.

Here, the first location may be a doctor's office and the second location may be a location other than the doctor's office such as a home of the user.

The distortion information generating unit 820 compares an iris color in the reference eyeball image and an iris color in the image for jaundice diagnosis to generate color distortion information indicating a degree of color distortion in the image for jaundice diagnosis.

As described above, the reason why the color distortion information is generated by comparing the iris colors is that even though the user has the jaundice symptom, the color of the iris does not change so that if the colors of the irises of the reference eyeball image and the image for jaundice diagnosis are different, it is assumed that the color distortion is generated and the degree of color distortion may be identified.

The image correcting unit 830 corrects the color distortion of the image for jaundice diagnosis based on the color distortion information to generate a correction image for jaundice diagnosis.

The diagnosis unit 840 diagnoses a jaundice symptom of the user using a correction image for jaundice diagnosis.

In this case, the diagnosis unit 840 may diagnose the jaundice symptom depending on whether the color of the white of the eye (sclera) of the eyeball of the user included in the correction image for jaundice diagnosis corresponds to jaundice.

FIG. 9 is a view for explaining an image based jaundice diagnosing apparatus according to another exemplary embodiment of the present disclosure.

Referring to FIG. 9, a jaundice diagnosing apparatus 900 according to another exemplary embodiment of the present disclosure includes a photographing unit 910, a jaundice diagnostic image acquisition control unit 920, a receiving unit 930, a distortion information generating unit 940, an image correcting unit 950, and a diagnosis unit 960. However, not all the illustrated components are required. The jaundice diagnosing apparatus 900 may be implemented by more components or less components than the illustrated components.

The photographing unit 910 photographs the specific body part of the user and the reference object together. A predetermined photographic parameter may be set in the photographing unit 910. For example, the predetermined photographing parameter may include a diaphragm value, whether to flash, a white balance condition, or the like.

Hereinafter, for the convenience of description, description will be made by limiting the reference object to a patch.

When an application for jaundice diagnosis is executed, the jaundice diagnostic image acquisition control unit 920 automatically drives the photographing unit 910 and analyzes an image displayed through the photographing unit 910 before photographing an image in real time to detect a patch and automatically photographs the image at the time when the patch is detected. In this case, the photographed image may be an image for jaundice diagnosis.

That is, the jaundice diagnostic image acquisition control unit 920 analyzes the image displayed through the photographing unit 910 before photographing the image in real time and detects an edge for each color area of the patch using an edge detecting algorithm. When the edge for the color area of the patch is detected, the jaundice diagnostic image acquisition control unit 920 determines that the image is an in-focus image to control the photographing unit 910 to automatically photograph the image at that time. Further, the edge for the color area of the patch is detected, the jaundice diagnostic image acquisition control unit 920 determines whether the detected edge is present in a predetermined range of the image. When the detected edge is present within the predetermined range, the jaundice diagnostic image acquisition control unit 920 determines that the image is an in-focus image and controls the photographing unit 910 to automatically photograph the image at that time.

As described above, the jaundice diagnostic image acquisition control unit 920 controls to photograph the specific body part of the user and the patch together in an in-focus state.

According to the exemplary embodiment, the user may photograph the image for jaundice diagnosis without performing a specific manipulation of pressing a photographing button to photograph the image for jaundice diagnosis.

The receiving unit 930 receives an image for jaundice diagnosis including the specific body part of the user and patch photographed by the photographing unit 910.

The distortion information generating unit 940 generates color distortion information representing a degree of color distortion of the patch included in the image for jaundice diagnosis. For example, the distortion information generating unit 940 compares a pixel value of a white color included in the patch and a pixel value of a reference color and generates the color distortion information based on a comparison result.

The image correcting unit 950 corrects the color distortion of the image for jaundice diagnosis based on the color distortion information to generate a correction image for jaundice diagnosis.

The diagnosis unit 960 diagnoses a jaundice symptom of the user using a correction image for jaundice diagnosis.

In the meantime, the jaundice diagnosing apparatus 900 according to the present disclosure may further include a storage unit (not illustrated) in which an application for jaundice diagnosis is stored. Further, in the storage unit, a pixel value of a reference color which is a reference for generating the color distortion information by the distortion information generating unit 940 is stored.

Further, the jaundice diagnosing apparatus 900 may further include a control unit (not illustrated) which controls operations of various components of the jaundice diagnosing apparatus 900. The control unit may store an application (or an applet) which allows the user to diagnose the jaundice in the storage unit and controls the application to be driven to diagnose the jaundice.

Further, the jaundice diagnosing apparatus 900 may further include a display unit (not illustrated) which displays various information related to an operation of the jaundice diagnosing apparatus 900. Specifically, the display unit may display various information such as an image acquired through the photographing unit 910 or a diagnostic result by the diagnosis unit. Such a display unit may be implemented through various display devices including an LCD, an LED, or the like.

Further, the jaundice diagnosing apparatus 900 may further include an input unit (not illustrated) for inputting information from the user. In the meantime, the input unit may be implemented by an input device such as a keypad or a touch panel and also implemented by various input devices in addition to the above-mentioned input device. Further, the input unit may be implemented by a touch screen type which is integrated with the display unit.

FIG. 11 is a view for explaining an image based jaundice diagnosis assisting apparatus according to an exemplary embodiment of the present disclosure.

Referring to FIG. 11, a jaundice diagnosis assisting apparatus 1100 according to an exemplary embodiment of the present disclosure includes a receiving unit 1110, a searching unit 1120, and an output unit 1130.

In this case, the jaundice diagnosis assisting apparatus 1100 may be a device mounted in a device of a doctor or a device of a doctor.

The receiving unit 1110 receives a correction image for jaundice diagnosis in which color distortion is corrected as an image obtained by photographing a specific body part of the user and a reference object.

In this case, the receiving unit 1110 may receive a correction image for jaundice diagnosis from a diagnosis server or a user device.

In another exemplary embodiment, the receiving unit 1110 may receive a jaundice diagnosis request which includes the correction image for jaundice diagnosis and requests the jaundice diagnosis for the user.

The searching unit 1120 searches medical history information of the user from a patient medical history DB including medical history information of a plurality of patients with jaundice.

In this case, the searching unit 1110 identifies a user using identification information (a phone number of a smart phone, and the like) of the user device which transmits the correction image for jaundice diagnosis and searches medical history information for the identified user.

In another exemplary embodiment, when the receiving unit 1110 receives the jaundice diagnosis request, the jaundice diagnosis request may include user identification information for identifying the user and the searching unit 1110 may search the medical history information for the user based on the user identification information included in the jaundice diagnosis request.

The output unit 1130 outputs the medical history information for the searched user and the correction image for jaundice diagnosis.

According to the present exemplary embodiment, a doctor is provided with the medical history information for the user corresponding to the correction image for jaundice diagnosis together with the correction image for jaundice diagnosis without directly searching the medical history information on the user so that convenience at the time of diagnosis is improved.

Desirably, the image based jaundice diagnosis assisting apparatus 1100 according to an exemplary embodiment of the present disclosure may further include an analyzing unit (not illustrated) which analyzes the correction image for jaundice diagnosis to generate an image analysis result indicating whether the user has a jaundice symptom and a depth of the jaundice. In this case, the output unit may output not only the medical history information of the user and the correction image for jaundice diagnosis, but also the image analysis result. Further, in another exemplary embodiment, the analyzing unit may further generate health risk degree information and in this case, the output unit may assist the jaundice diagnosis of the doctor by outputting the health risk degree information.

For now, the present invention has been described with reference to the exemplary embodiments. It is understood to those skilled in the art that the present invention may be implemented as a modified form without departing from an essential characteristic of the present invention. Therefore, the disclosed exemplary embodiments may be considered by way of illustration rather than limitation. The scope of the present disclosure is presented not in the above description but in the claims and it may be interpreted that all differences within an equivalent range thereto may be included in the present disclosure.

What is claimed is:

1. A method for diagnosing jaundice based on an image by a jaundice diagnosing apparatus, the method comprising:
   receiving an image for jaundice diagnosis obtained by photographing a specific body part of a user and a reference object;
   generating color distortion information representing a degree of color distortion of the reference object included in the image for jaundice diagnosis;
   generating a correction image for jaundice diagnosis by correcting the color distortion of the image for jaundice diagnosis based on the color distortion information; and
   diagnosing a jaundice symptom of the user using the correction image for jaundice diagnosis,
   wherein the reference object is an eye patch and the eye patch is configured by a single area having a white color or a plurality of areas having different colors.

2. The method according to claim 1, wherein the diagnosing of a jaundice symptom of the user includes:

transmitting a jaundice diagnosis request which includes the correction image for jaundice diagnosis and requests the jaundice diagnosis for the user to a diagnosis server; and receiving a jaundice diagnosis result which is a diagnosis result for the jaundice diagnosis request from the diagnosis server.

3. The method according to claim 2, wherein the jaundice diagnosis result is determined based on the image analysis result for the correction image for jaundice diagnosis and also determined further selectively based on at least one of medical history information of the user and medical treatment information of others with a jaundice symptom.

4. The method according to claim 3, wherein the jaundice diagnosis result further includes health risk information indicating whether the jaundice symptom of the user is risky for health, based on the correlation between the disease of the user predicted based on at least one of the medical history information of the user and the medical treatment information of others and the image analysis result.

5. The method according to claim 1, wherein when the reference object is a white object, in the generating of color distortion information, color temperature difference information which is a difference value between a first color temperature of the reference object in a reference image obtained by photographing the reference object under a previously stored reference light source and a second color temperature of the reference object included in the image for jaundice diagnosis is generated and in the generating of a correction image for jaundice diagnosis, the color temperature of the image for jaundice diagnosis is corrected such that the color temperature of the reference object of the image for jaundice diagnosis is equal to the first color temperature based on the color temperature difference information to generate a correction image for jaundice diagnosis.

6. The method according to claim 1, wherein the specific body part of the user include at least one of a face and an eyeball of the user.

7. The method according to claim 1, further comprising:
outputting a user interface for photographing the image for jaundice diagnosis,
wherein in the receiving of an image for jaundice diagnosis, the image photographed based on a photographing guideline provided on the user interface in real time is received.

8. The method according to claim 1, wherein the image for jaundice diagnosis is an image in which the reference object is worn or attached on the specific body part of the user.

9. The method according to claim 1, wherein the eye patch is configured by a plurality of areas having a white color and at least one different color.

10. The method according to claim 9, wherein in the eye patch, a pattern in which a first area and a second area having the same color are alternately disposed with a white area therebetween is formed.

11. The method according to claim 9, wherein the eye patch is attached on a face within a predetermined distance from the eye of the user or attached to a tool within a predetermined distance from the eye when a tool is used to widen a sclera of the eye.

12. The method according to claim 1, further comprising:
before the receiving of an image for jaundice diagnosis, analyzing an image displayed through a camera equipped in the jaundice diagnosing apparatus in real time to automatically photograph an image at a time when the reference object is detected,
wherein the photographed image is an image for jaundice diagnosis.

13. The method according to claim 1, wherein the color distortion information is generated based on at least one of illumination of environment in which the image for jaundice diagnosis is photographed, a photographic related setting value of a user device which photographs the image for jaundice diagnosis and a lens aberration of a lens mounted on the user device.

14. The method according to claim 1, wherein when a reference image obtained by photographing the reference object under a reference light source which is stored in advance has a YCbCr format and the image for jaundice diagnosis has an RGB format,
the generating of color distortion information includes:
generating a converted image for jaundice diagnosis by converting the image for jaundice diagnosis into the YCbCr format; and
calculating a first luminance distribution function which is a cumulative probability density function for a luminance value Y of the entire pixels belonging to a converted image for jaundice diagnosis to generate the color distortion information,
in the generating of a correction image for jaundice diagnosis, the correction image for jaundice diagnosis is generated by correcting the converted image for jaundice diagnosis corresponding to the first luminance distribution function to have a second luminance distribution function which is a cumulative probability density function for a luminance value Y of entire pixels belonging to the reference image.

15. An image based jaundice diagnosing apparatus, comprising:
a receiver configured to receive an image for jaundice diagnosis obtained by photographing a specific body part of a user and a reference object; and
a processor configured to:
generate color distortion information representing a degree of color distortion of the reference object included in the image for jaundice diagnosis;
correct the color distortion of the image for jaundice diagnosis based on the color distortion information to generate a correction image for jaundice diagnosis; and
diagnose a jaundice symptom of the user using the correction image for jaundice diagnosis,
wherein the reference object is an eye patch and the eye patch is configured by a single area having a white color or a plurality of areas having different colors.

16. The image based jaundice diagnosing apparatus according to claim 15, wherein the eye patch is configured by a plurality of areas having a white color and at least one different color.

* * * * *